United States Patent [19]

Rentzea et al.

[11] Patent Number: 4,960,774
[45] Date of Patent: Oct. 2, 1990

[54] CYCLIC AMINES AND FUNGICIDES CONTAINING THEM

[75] Inventors: Costin Rentzea, Heidelberg; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 363,087

[22] Filed: Jun. 8, 1989

[30] Foreign Application Priority Data

Jun. 8, 1988 [DE] Fed. Rep. of Germany ........ 3819465

[51] Int. Cl.$^5$ ................ C07D 211/14; C07D 295/084; A01N 43/40; A01N 43/84
[52] U.S. Cl. ................... 514/239.2; 514/315; 544/158; 544/177; 546/248
[58] Field of Search ................ 544/158, 177; 546/248; 514/239.2, 315

[56] References Cited

U.S. PATENT DOCUMENTS 4,650,865  3/1987  Lange et al. .................. 544/174

Primary Examiner—Mary C. Lee
Assistant Examiner—Jacqueline Haley
Attorney, Agent, or Firm—Oblon, Spivak, McClelland, Maier & Neustadt

[57] ABSTRACT

Amines of the general formula I

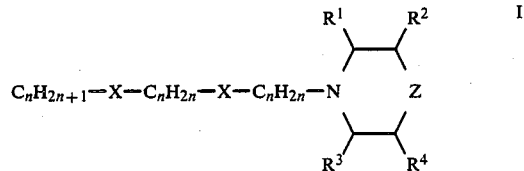

where n is an integer from 2 to 10, X is oxygen or sulfur, Z is oxygen or CH—$R_5$, and $R^1$, $R^2$, $R^3$, $R^4$ and $R^5$ are identical or different and are each hydrogen or alkyl, salts thereof, and fungicides containing these compounds.

5 Claims, No Drawings

CYCLIC AMINES AND FUNGICIDES CONTAINING THEM

The present invention relates to novel cyclic amines, processes for their preparation, their use as fungicides, fungicides which contain the novel active ingredients, processes for the preparation of such fungicides and methods for controlling harmful fungi with these fungicides.

It is known that N-tridecyl-2,6-dimethylmorpholine can be used as a fungicide (DE No. 1,164,152).

We have found that compounds of the formula I

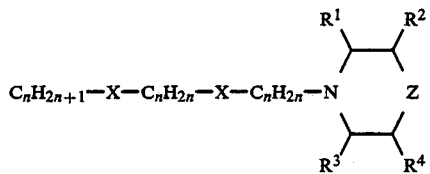

where the $C_nH_{2n+1}$ and $C_nH_{2n}$ units are straight-chain or branched and n is from 2 to 10 (2, 3, 4, 5, 6, 7, 8, 9 or 10), the individual values of n being identical or different, X is oxygen or sulfur, Z is oxygen or CH—$R^5$ and $R^1$, $R^2$, $R^3$, $R^4$ and $R^5$ are identical or different and independent of one another are each hydrogen or $C_1$- or $C_2$-alkyl (methyl or ethyl), and their salts have excellent activity against harmful fungi and are very well tolerated by plants.

The novel amines of the formula I may contain chiral centers. They are generally obtained as racemates and may be obtained as diastereomer mixtures. In the case of some of the novel compounds, diastereomers can be isolated in pure form, for example by column chromatography or on the basis of solubility differences. Pure racemates and enantiomers can be obtained from such purified diastereomers by known methods. All these compounds and mixtures are embraced by the present invention. Regarding the use of the novel amines as fungicides, both the pure diastereomers or enantiomers and their mixtures obtained in the synthesis are suitable. The latter are preferably used.

The amines of the formula I can be prepared by (a) reacting a compound of the formula II with an amine of the formula III

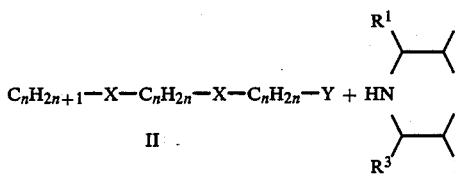

where n, X, Z and $R^{1-5}$ have the abovementioned meanings and Y is a nucleophilically displaceable leaving group, for example halogen (Cl or Br) or alkyl- or arylsulfonyl, or (b) reacting an alkylating agent of the formula IV with an amine of the formula V

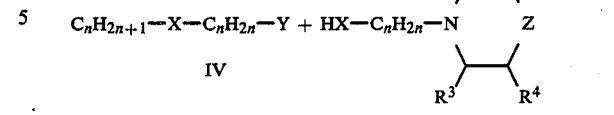

where X, Z, n and $R^{1-5}$ have the abovementioned meanings, or (c) reacting an alcohol or thiol of the formula IV with an amine of the formula VII

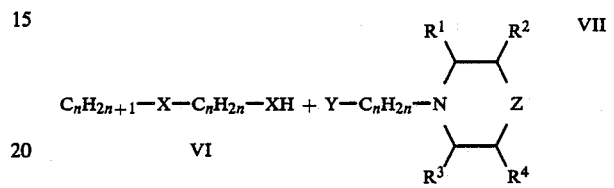

where X, Y, Z, n and $R^{1-5}$ have the abovementioned meanings, in the presence or absence of a solvent or diluent and/or of an inorganic or organic base and/or of a reaction accelerator, and, if required, converting the resulting compound into its salts.

Examples of suitable solvents or diluents for all three process variants (a), (b) and (c) are halohydrocarbons, in particular chlorohydrocarbons, e.g. tetrachloroethylene, 1,1,2,2- and 1,1,1,2-tetrachlorethane, dichloropropane, methylene chloride, dichlorobutane, chloroform, chloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, 1,2-cis-dichloroethylene, o-, p- and m-dibromobenzene, o-, m- and p-chlorotoluene and 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and β,β,β'-dichlorodiethyl ether; nitrohydrocarbons, such as nitromethane, nitroethane, nitrobenzene, o-, m- and p-chloronitrobenzene and o-nitrotoluene; nitriles, such as acetonitrile, butyronitrile, isobutyronitrile, benzonitrile and m-chlorobenzonitrile; aliphatic and cycloaliphatic hydrocarbons, e.g. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, e.g. ethyl acetate, ethyl acetoacetate and isobutyl acetate; amides, e.g. formamide, methylformamide and dimethylformamide; ketones, e.g. acetone and methyl ethyl ketone, and, if desired, also water and mixtures of these. Compounds of the formulae III, IV and V in excess can also be used as solvents. Advantageously, the solvent is used in an amount of from 100 to 2,000, preferably from 200 to 700%, by weight, based on starting material II.

All conventional acid acceptors can be used as inorganic or organic bases for the reaction to given compounds of the formula I. These preferably include tertiary amines, alkaline earth metal compounds and mixtures of these. However, zinc compounds can also be used. Examples of suitable basic compounds are the following: potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, sodium formate, sodium acetate, trimethylamine, triethylamine, tripropylamine, triisopropylamine, tributylamine, triisobutylamine, tri-sec-butylamine, tri-tert-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-dimethyl-p-aminopyridine, N,N-diethyl-p-aminopyridine, N-methylpyrrolidine, N-ethylpyrrolidone, N-methylpiperidine, N-ethylpiperidine, N-methylpyrrolidine, N-ethylpyrrolidine, N-methylimidazole, N-ethylimidazole, N-methylmorpholine, N-ethylmorpholine, N-methylhexamethyleneimine, N-ethylhexamethyleneimine, pyridine, quinoline, alpha-picoline, gamma-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

Advantageously, the acid acceptor is used in an amount which is from 80 to 120% of the stoichiometric amount, based on the starting material II, IV or VI.

Preferred reaction accelerators are metal halides, such as sodium iodide or potassium iodide.

All organic and inorganic acids are suitable for salt formation with compounds of the formula I (acid addition salts), provided that the form phytophysiologically tolerated salts. Examples are chlorides, bromides, iodides, sulfates, phosphates, acetates, oxalates, fumarates, malonates, alkylsulfonates, arylsulfonates and dodecylbenzenesulfonates.

The salts are obtained by combining the appropriate acid with a free amine of the formula I, if necessary in an inert solvent, separating off the solvent and if necessary recrystallizing the residue.

The starting materials of the formula II, where Y is chlorine or bromine, are novel. They can be prepared by a conventional method.

They can be obtained, for example, by reacting (d) an alcohol or thiol of the formula IV with a 1, omegadihalo derivative of the formula VIII Y—C$_n$H$_{2n}$—Y    VIII where n and Y have the abovementioned meanings, in the presence or absence of one or more solvents and diluents and/or inorganic bases and/or a phase transfer catalyst.

Reaction (d) is advantageously carried out in solvents which are inert with respect to the reactants, for example toluene, 1,2-dimethoxyethane, tetrahydrofuran, dioxane, methylene chloride, dimethylformamide, water or a mixture of these. The compounds of the formula VIII in excess can also be used as solvents.

Examples of suitable acid acceptors are inorganic bases, such as hydrides, hydroxides, carbonates, borates and phosphates of alkali metals and alkaline earth metals, for example sodium hydride, sodium hydroxide, potassium hydroxide, calcium oxide, sodium carbonate, potassium carbonate, sodium bicarbonate, potassium bicarbonate, magnesium carbonate, calcium carbonate, barium carbonate, sodium phosphates and potassium phosphates.

Preferred phase transfer catalysts are quarternary ammonium and phosphonium salts, such as tetrabutylammonium chloride, bisulfate, hydroxide, bromide and iodide, benzyltriethylammonium chloride, cetyltrimethylammonium chloride or benzyltriphenylphosphonium chloride, and crown ethers, such as 12-crown-4, 15-crown-5, 18-crown-6, dibenzo-18-crown-6 or dicylcohexano-18-crown-6.

The reactions (a), (b), (c) and (d) are generally carried out at from 0° to 100° C., under atmospheric or superatmospheric pressure, continuously or batchwise.

Intermediates such as the alkylating reagents IV, the amines III, V and VII and the alcohols or thiols VI are known.

METHOD 1

Preparation of the intermediate

A mixture of 98.5 g (0.675 mole) of 1-isobutoxybutan-2-ol, 350 ml of 1,4-dichlorobutane, 10 g of tetrabutylammonium bisulfate and 250 g of 50% strength by weight aqueous sodium hydroxide solution is heated at 50° C. for 24 hours while stirring vigorously. 1 l of water is then added to the mixture, which is extracted with four times 300 ml of methylene chloride. The combined extracts are extracted by shaking with five times 200 ml of water, dried over magnesium sulfate and subjected to fractional distillation under reduced pressure.

81.2 g (51% of theory) of 1-isobutoxy-2-(440 -chlorobutoxy)-butane are obtained as a colorless liquid of boiling point 142°–143° C./20 mbar and $n_D^{22} = 1.4361$.

EXAMPLE 1

Cis-2,6-dimethyl-4-{4'-[1''-isobutroxy-2''-butoxy]-but-1'-yl}-morpholine

A mixture of 20 g (0.08 mols) of 1-isobutoxy-2-(4'-chloro-1'-butoxy)-butane, 70 ml of cis-2,6-dimethylmorpholine and 2 g of potassium iodide is heated at 90° C. for 24 hours while stirring. The reaction mixture is cooled to 10° C., after which 100 ml of ether and 50 ml of 50% strength aqueous sodium hydroxide solution are added to the mixture in succession. The organic phase is dried over Na$_2$SO$_4$ and subjected to fractional distillation under reduced pressure.

20 g (80% theory) of the title compound were obtained as a colorless oil of boiling point 122°–123° C./0.1 mbar and $n_D^{25} = 1.4462$.

TABLE 1

| Intermediates of the formula C$_n$H$_{2n+1}$—X—C$_n$H$_{2n}$—X—C$_n$H$_{2n}$—Y | | | | | | |
|---|---|---|---|---|---|---|
| C$_n$H$_{2n+1}$ | X | C$_n$H$_{2n}$ | X | C$_n$H$_{2n}$ | Y | Refractive index or boiling point (°C./mbar) |
| n-propyl | O | —(CH$_2$)$_2$— | O | —(CH$_2$)$_4$— | Cl | 78–90/0.2 |
| n-propyl | S | —(CH$_2$)$_2$— | O | —(CH$_2$)$_6$— | Cl | 91–92/0.15 |
| isopropyl | O | —(CH$_2$)$_2$— | O | —(CH$_2$)$_4$— | Cl | 73–75/0.2 |

TABLE 1-continued

Intermediates of the formula $C_nH_{2n+1}-X-C_nH_{2n}-X-C_nH_{2n}-Y$

| $C_nH_{2n+1}$ | X | $C_nH_{2n}$ | X | $C_nH_{2n}$ | Y | Refractive index or boiling point (°C./mbar) |
|---|---|---|---|---|---|---|
| isopropyl | S | $-(CH_2)_2-$ | O | $-(CH_2)_6-$ | Cl | $n_D^{22}$ 1.4729 |
| isopropyl | O | $-CH_2-CH(CH_3)-$ | O | $-(CH_2)_4-$ | Cl | 80–84/0.3 |
| isopropyl | O | $-CH_2-CH(CH_3)-$ | O | $-(CH_2)_6-$ | Cl | 95–97/0.3 |
| isopropyl | O | $-CH_2-CH(C_2H_5)-$ | O | $-(CH_2)_4-$ | Cl | 93–96/0.3 |
| n-butyl | O | $-CH_2-CH(CH_3)-$ | O | $-(CH_2)_4-$ | Cl | 88–91/0.2 |
| n-butyl | O | $-CH(CH_3)-CH_2-$ | O | $-(CH_2)_4-$ | Cl | 92–96/0.3 |
| n-butyl | S | $-CH_2-CH(CH_3)-$ | O | $-(CH_2)_4-$ | Cl | 91–94/0.1 |
| isobutyl | O | $-(CH_2)_2-$ | O | $-(CH_2)_6-$ | Cl | $n_D^{22}$ 1.4410 |
| isobutyl | S | $-(CH_2)_2-$ | O | $-(CH_2)_6-$ | Cl | 89–92/0.2 |
| isobutyl | O | $-CH_2-CH(CH_3)-$ | O | $-(CH_2)_4-$ | Cl | 136–139/20 |
| isobutyl | O | $-CH_2-CH(CH_3)-$ | O | $-(CH_2)_6-$ | Cl | $n_D^{22}$ 1.4382 |
| isobutyl | O | $-CH_2-CH(C_2H_5)-$ | O | $-(CH_2)_3-$ | Cl | 139–142/20 |
| isobutyl | O | $-CH_2-CH(C_2H_5)-$ | O | $-(CH_2)_4-$ | Cl | $n_D^{23}$ 1.4361 |
| isobutyl | S | $-CH_2-CH(C_2H_5)-$ | O | $-(CH_2)_4-$ | Cl | 145–147/20 |
| isobutyl | O | $-CH_2-CH(C_3H_7)-$ | O | $-(CH_2)_4-$ | Cl | $n_D^{22}$ 1.4381 |
| isobutyl | O | $-CH_2-CH(C_3H_7)-$ | O | $-(CH_2)_5-$ | Cl | $n_D^{22}$ 1.4381 |
| isobutyl | O | $-CH_2-CH(C_3H_7)-$ | O | $-(CH_2)_6-$ | Cl | 148–150/20 |
| isobutyl | O | $-CH_2-CH(C_6H_{13})-$ | O | $-(CH_2)_4-$ | Cl | $n_D^{23}$ 1.4427 |
| isobutyl | O | $-CH_2-CH(CH_3)-$ | O | $-(CH_2)_8-$ | Cl | 151–153/17 |
| isobutyl | O | $-CH_2-CH(CH_3)-$ | O | $-(CH_2)_8-$ | Cl | 150–154/17 |
| n-hexyl | O | $-CH_2-CH(CH_3)-$ | O | $-(CH_2)_4-$ | Cl | 110–113/0.2 |
| n-hexyl | O | $-CH_2-CH(C_2H_5)-$ | O | $-(CH_2)_4-$ | Cl | 112–115/0.2 |
| 2,2-dimethylpropyl-1- | O | $-(CH_2)_2-$ | O | $-(CH_2)_4-$ | Cl | 109–111/0.2 |
| 2,2-dimethylpropyl-1- | O | $-CH_2(CH_3)-CH_2-$ | O | $-(CH_2)_6-$ | Cl | 120–122/0.3 |
| 3,3-dimethylbutyl-1- | O | $-(CH_2)_4-$ | O | $-(CH_2)_6-$ | Cl | 123–126/0.2 |
| 3,3-dimethylbutyl-1- | O | $-CH_2-CH(CH_3)-$ | O | $-(CH_2)_4-$ | Cl | 110–112/0.2 |
| 3,3-dimethylbutyl-1- | O | $-CH_2-CH(C_2H_5)-$ | O | $-(CH_2)_4-$ | Cl | 113–116/0.2 |
| 2,4-dimethylpentyl-1- | O | $-(CH_2)_2-$ | O | $-(CH_2)_4-$ | Cl | 150–152/20 |
| 2,4-dimethylpentyl-1- | O | $-CH_2CH(C_2H_5)-$ | O | $-(CH_2)_4$ | Cl | 112–115/0.2 |
| 3-heptyl | O | $-CH(CH_3)CH_2$ | O | $-(CH_2)_4-$ | Cl | $n_D^{23}$ 1.4410 |
| 2-ethyl-4-methyl pentyl-1 | O | $-CH_2-CH(C_2H_5)-$ | O | $-(CH_2)_4-$ | Cl | 110–113/0.2 |
| 2-ethyl-4-methyl pentyl-1 | O | $-CH_2-CH(C_2H_5)-$ | O | $-(CH_2)_6-$ | Cl | 119–123/0.2 |
| 2-ethylhexyl-1 | O | $-CH_2-CH(C_2H_5)-$ | O | $-(CH_2)_6-$ | Cl | 158–160/17 |
| 2-ethylhexyl-1 | O | $-CH_2-CH(CH_3)-$ | O | $-(CH_2)_4-$ | Cl | 147–149/17 |
| n-octyl | O | $-CH_2-CH(C_2H_5)-$ | O | $-(CH_2)_4-$ | Cl | 149–153/20 |
| n-octyl | O | $-CH_2-CH(C_2H_5)-$ | O | $-(CH_2)_6-$ | Cl | 121–124/0.3 |
| n-decyl | O | $-CH_2-CH(CH_3)-$ | O | $-(CH_2)_4-$ | Cl | 125–126/0.1 |
| n-decyl | S | $-CH_2-CH(CH_3)-$ | O | $-(CH_2)_4-$ | Cl | 131–135/0.1 |
| n-decyl | O | $-CH_2-CH(C_2H_5)-$ | O | $-(CH_2)_4-$ | Cl | 130–134/0.2 |

TABLE 2

Compounds of the general formula I
The compounds listed below may be obtained as in Example 1 by appropriate selection of the starting materials and the process conditions.

| Ex. No. | $C_nH_{2n+1}-X-C_nH_{2n}-X-C_nH_{2n}$ | $R^1$ | $R^2$ | $R^3$ | $R^4$ | Z | Refractive index or bp. (°C./mbar) |
|---|---|---|---|---|---|---|---|
| 2 | $CH_3(CH_2)_2-O-(CH_2)_4-$ | H | $CH_3$ | H | $CH_3$ | O | 133–136/0.3 |
| 3 | $(CH_3)_2CH-O-(CH_2)_2-O-(CH_2)_4-$ | H | $CH_3$ | H | $CH_3$ | O | 128–131/0.2 |
| 4 | $(CH_3)_2CH-O-(CH_2)_2-O-(CH_2)_4-$ | H | $CH_3$ | H | $CH_3$ | O | 129–132/0.2 |
| 5 | $(CH_3)_2CH-O-(CH_2)_2-O-(CH_2)_4-$ | H | $CH_3$ | H | $CH_3$ | O | 125–128/0.1 |
| 6 | $(CH_3)_2CH-O-(CH_2)_2-O-(CH_2)_6-$ | H | $CH_3$ | H | $CH_3$ | O | 132–135/0.2 |
| 7 | $(CH_3)_2CH-O-(CH_2)_2-O-(CH_2)_6-$ | H | $CH_3$ | H | $CH_3$ | O | 133–136/0.2 |
| 8 | $(CH_3)_2CH-O-(CH_2)_2-O-(CH_2)_4-$ | H | $CH_3$ | H | $CH_3$ | O | 142–144/0.3 |
| 9 | $(CH_3)_2CH-O-(CH_2)_2-O-(CH_2)_6-$ | H | $CH_3$ | H | $CH_3$ | O | $n^{22}$ 1.4742 |
| 10 | $(CH_3)_2CH-CH_2-O-(CH_2)_2-O-(CH_2)_4-$ | H | $CH_3$ | H | $CH_3$ | O | 120–124/0.2 |
| 11 | $(CH_3)_2CH-CH_2-O-CH_2-CH(CH_3)-O-(CH_2)_4-$ | H | $CH_3$ | H | $CH_3$ | O | 121–125/0.1 |
| 12 | $(CH_3)_2CH-CH_2-O-CH_2-CH(CH_3)-O-(CH_2)_4-$ | H | $CH_3$ | H | $CH_3$ | O | 122–126/0.2 |
| 13 | $(CH_3)_2CH-CH_2-O-CH_2-CH(CH_3)-O-(CH_2)_4-$ | H | $CH_3$ | H | $CH_3$ | O | 128–130/0.3 |
| 14 | $(CH_3)_2CH-CH_2-O-CH_2-CH(CH_3)-O-(CH_2)_4-$ | H | $CH_3$ | H | $CH_3$ | O | 125–128/0.2 |
| 15 | $(CH_3)_2CH-CH_2-O-CH_2-CH(CH_3)-O-(CH_2)_4-$ | H | $CH_3$ | H | $CH_3$ | O | 129–133/0.3 |
| 16 | $(CH_3)_2CH-CH_2-O-(CH_2)_2-O-(CH_2)_6-$ | H | $CH_3$ | H | $CH_3$ | O | $n^{25}$ 1.4501 |
| 17 | $(CH_3)_2CH-CH_2-O-(CH_2)_2-O-(CH_2)_6-$ | H | $CH_3$ | H | $CH_3$ | O | 142–145/0.1 |
| 18 | $(CH_3)_2CH-CH_2-O-CH_2-CH(CH_3)-O-(CH_2)_6-$ | H | $CH_3$ | H | $CH_3$ | O | $n^{22}$ 1.4493 |
| 19 | $(CH_3)_2CH-CH_2-O-CH_2-CH(CH_3)-O-(CH_2)_6-$ | H | $CH_3$ | H | $CH_3$ | O | 122–125/0.1 |
| 20 | $(CH_3)_2CH-CH_2-O-CH_2-CH(CH_3)-O-(CH_2)_6-$ | H | $CH_3$ | H | $CH_3$ | O | 128–131/0.2 |
| 21 | $(CH_3)_2CH-CH_2-O-CH_2-CH(CH_3)-O-(CH_2)_6-$ | H | $CH_3$ | H | $CH_3$ | O | 123–126/0.1 |
| 22 | $(CH_3)_2CH-CH_2-O-CH_2-CH(CH_3)-O-(CH_2)_6-$ | H | $CH_3$ | H | $CH_3$ | O | 135–137/0.2 |
| 23 | $(CH_3)_2CH-CH_2-O-CH_2-CH(C_3H_7)-O-(CH_2)_4-$ | H | $CH_3$ | H | $CH_3$ | O | $n^{23}$ 1.4486 |
| 24 | $(CH_3)_2CH-CH_2-O-CH_2-CH(C_3H_7)-O-(CH_2)_6-$ | H | $CH_3$ | H | $CH_3$ | O | $n^{23}$ 1.4509 |
| 25 | $(CH_3)_2CH-CH_2-O-CH_2-CH(C_6H_{13})-O-(CH_2)_4-$ | H | $CH_3$ | H | $CH_3$ | O | 157–160/0.3 |
| 26 | $(CH_3)_2CH-CH_2-O-CH_2-CH(CH_3)-O-(CH_2)_8-$ | H | $CH_3$ | H | $CH_3$ | O | 156–159/0.2 |

TABLE 2-continued

Compounds of the general formula I
The compounds listed below may be obtained as in Example 1 by appropriate selection
of the starting materials and the process conditions.

| Ex. No. | $C_nH_{2n+1}$—X—$C_nH_{2n}$—X—$C_nH_{2n}$ | $R^1$ | $R^2$ | $R^3$ | $R^4$ | Z | Refractive index or bp. (°C./mbar) |
|---|---|---|---|---|---|---|---|
| 27 | $CH_3$—$(CH_2)_5$—O—$CH_2$—$CH(CH_3)$—O—$(CH_2)_4$— | H | $CH_3$ | H | $CH_3$ | O | 146–148/0.2 |
| 28 | $CH_3$—$(CH_2)_5$—O—$CH_2$—$CH(CH_3)$—O—$(CH_2)_4$— | H | $CH_3$ | H | $CH_3$ | O | 140–142/0.2 |
| 29 | $CH_3$—$(CH_2)_5$—O—$CH_2$—$CH(C_2H_5)$—O—$(CH_2)_4$ | H | $CH_3$ | H | $CH_3$ | O | 140–143/0.1 |
| 30 | $CH_3$—$(CH_2)_5$—O—$CH_2$—$CH(C_2H_5)$—O—$(CH_2)_4$ | H | $CH_3$ | H | $CH_3$ | O | 148–151/0.2 |
| 31 | $(CH_3)_3C$—$CH_2$—O—$(CH_2)_2$—O—$(CH_2)_4$— | H | $CH_3$ | H | $CH_3$ | O | 122–125/0.1 |
| 32 | $(CH_3)_3C$—$CH_2$—O—$CH_2(CH_3)$—$CH_2$—O—$(CH_2)_6$— | H | $CH_3$ | H | $CH_3$ | O | 147–149/0.3 |
| 33 | $(CH_3)_3C$—$CH_2$—O—$(CH_2)_4$—O—$(CH_2)_6$— | H | $CH_3$ | H | $CH_3$ | O | 157–160/0.2 |
| 34 | $(CH_3)_3C$—$CH_2$—O—$CH_2CH(CH_3)$—O—$(CH_2)_4$— | H | $CH_3$ | H | $CH_3$ | O | 125–128/0.1 |
| 35 | $(CH_3)_3C$—$CH_2$—$CH_2$—O—$CH_2CH(C_2H_5)$—O—$(CH_2)_4$— | H | $CH_3$ | H | $CH_3$ | O | 127–130/0.1 |
| 36 | $(CH_3)_2CH$—$CH_2$—$CH(CH_3)$—$CH_2$—O—$(CH_2)_2$—O—$(CH_2)_4$ | H | $CH_3$ | H | $CH_3$ | O | 147–150/0.2 |
| 37 | $(CH_3)_2CH$—$CH_2$—$CH(CH_3)$—$CH_2$—O—$CH_2$—$CH(C_5H_5)$—O—$(CH_2)_4$— | H | $CH_3$ | H | $CH_3$ | O | 155–158/0.3 |
| 38 | $CH_3$—$(CH_2)_2$—$CH(C_3H_7)$—O—$CH(CH_3)CH_2$—O—$(CH_2)_4$— | H | $CH_3$ | H | $CH_3$ | O | $n^{22}$ 1.4502 |
| 39 | $(CH_3)_2$—$CH_2$—$CH(C_2H_5)$—$CH_2$—O—$CH_2CH(C_2H_5)$—O—$(CH_2)_4$— | H | $CH_3$ | H | $CH_3$ | O | 161–163/0.3 |
| 40 | $(CH_3)_2$—$CH_2$—$CH(C_2H_5)$—$CH_2$—O—$CH_2CH(C_2H_5)$—O—$(CH_2)_4$— | H | $CH_3$ | H | $CH_3$ | O | 147–149/0.3 |
| 41 | $CH_3$—$(CH_2)_3$—$CH(C_2H_5)$—$CH_2$—O—$CH_2CH(CH_3)$—O—$(CH_2)_4$— | H | $CH_3$ | H | $CH_3$ | O | 153–155/0.2 |
| 42 | $CH_3$—$(CH_2)_3$—$CH(C_2H_5)$—$CH_2$—O—$CH_2CH(CH_3)$—O—$(CH_2)_4$— | H | $CH_3$ | H | $CH_3$ | O | 140–142/0.2 |
| 43 | $CH_3$—$(CH_2)_3$—$CH(C_2H_5)$—$CH_2$—O—$CH_2$—$CH(C_2H_5)$—O—$(CH_2)_4$— | H | $CH_3$ | H | $CH_3$ | O | 145–147/0.2 |
| 44 | $CH_3$—$(CH_2)_3$—$CH(C_2H_5)$—$CH_2$—O—$CH_2$—$CH(C_2H_5)$—O—$(CH_2)_4$— | H | $CH_3$ | H | $CH_3$ | O | 155–158/0.2 |
| 45 | $CH_3$—$(CH_2)_7$—O—$CH_2$—$CH(C_2H_5)$—O—$(CH_2)$—O—$(CH_2)_4$— | H | $CH_3$ | H | $CH_3$ | O | 156–158/0.2 |
| 46 | $CH_3$—$(CH_2)_7$—O—$CH_2$—$CH(C_2H_5)$—O—$(CH_2)_6$— | H | $CH_3$ | H | $CH_3$ | O | 149–153/0.1 |
| 47 | $CH_3$—$(CH_2)_7$—O—$CH_2$—$CH(C_2H_5)$—O—$(CH_2)_6$— | H | $CH_3$ | H | $CH_3$ | O | 140–142/0.1 |
| 48 | $CH_3$—$(CH_2)_9$—O—$CH_2$—$CH(CH_3)$—O—$(CH_2)_4$— | H | $CH_3$ | H | $CH_3$ | O | 147–149/0.2 |
| 49 | $CH_3$—$(CH_2)_9$—S—$CH_2$—$CH(C_2H_5)$—O—$(CH_2)_4$— | H | $CH_3$ | H | $CH_3$ | O | 165–169/0.1 |
| 50 | $CH_3$—$(CH_2)_9$—O—$CH_2$—$CH(C_2H_5)$—O—$(CH_2)_4$— | H | $CH_3$ | H | $CH_3$ | O | 150–156/0.1 | in general terms, the novel compounds are extremely effective on a broad spectrum of phytopathogenic fungi, in particular those from the Ascomycetes, Basidiomycetes and Deuteromycetes classes, but also from the Phycomycetes class. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeams, coffee, sugar cane, fruit and ornamentals in horticulature and viticulture, and in vegetables such as cucumbers, beans and cucurbits.

The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Venturia inaequalis (scab) in apples,
Septoria nodorum in wheat,
Botrytis cinerea (gray mold) in strawberries andd grapes,
Pseudocercosporella herpotrichoides in wheat and barley,
Pyricularia oryzae in rice,
Alternaria solani in potatoes and tomatoes,
Fusarium and Verticillium species in various plants,
Plasmopara viticola in grapes,
Pyrenophora teres in barley.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethlformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 1 is mixed with 10 parts by weight of N-methyl-α-pyrrolidone. A mixture is obtained which is suitable for application in the form of very fine drops.

II. 20 parts by weight of compound no. 23 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of caster oil. By pouring the solution into water and uniformly distributing it therein, an aqueous dispersion is obtained.

III. 20 parts by weight of compound no. 1 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 23 is dissolved in a mixture consisting of 25 parts by weight of cyclohexanol, 65 parts by weight of a mineral oil fraction having a boiling point between 210° and 200° C., and 10 parts by weight of the adduct of 40 moles of ethylene oxide and 1 mole of caster oil. By pouring the solution into water and uniformly distributing it therein, an aqueous dispersion is obtained.

V. 80 parts by weight of compound no. 1 is well mixed with 3 parts by weight of the sodium salt of diisobutylnaphthalene-α-sulfonic acid, 10 parts by weight of the sodium of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 23 is intimately mixed with 97 parts by weight of particulate kaolin. A dust is obtained containing 3% by weight of the active ingredient.

VII. 30 parts by weight of compound no. 1 is intimately mixed with a mixture consisting of 92 parts by weight of powdered silica gel and 8 parts by weight of paraffin oil which has been sprayed onto the surface of this silica gel. A formation of the active ingredient is obtained having good adherence.

VIII. 40 parts by weight of compound no. 23 is intimately mixed with 10 parts of the sodium salt off a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 1 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'propylenebisdithiocarbamate,
zinc N,N'-propylenebisdithiocarbamate and
N,N'-polypropylenebis(thiocarbamyl) disulfide;

nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;

heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide, N-dichlorofluoromethylthio-N', N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
3,2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamine-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole.
1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolyl-urea,
1-(4-chlorophenoxy)-3,3-dimethyl-1-(1H-1,2,4-triazole-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide, hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole, and
2,4-difluoro-α-(1H-1,2,4-triazol-1-ylmethyl)-benzhydryl alcohol.

Use example for comparison purposes, N-tridecyl-2,6-dimethyl-morpholine (A) disclosed in DE No. 1,164,152 was used.

action on *Pseudocercosporella herpotrichoides*

Wheat plants of the "Frühgold" variety were sprayed to runoff at the one-leaf stage with aqueous formulations containing (dry basis) 80% of active ingredient and 20% of emulsifier. After 24 hours, these plants were inoculated with a spore suspension of pseudocercosporella herpotrichoides. To provide optimum development conditions for the disease, the plants were then set up for one week in a climatic cabinet at 16°–18° C. and a relative humidity of more than 95%. The plants were then cultivated for a further two weeks in the greenhouse at 15°–17° C. The spread of the disease was then assessed on the lower portion of the plant stem.

The results show that active ingredient 1 and 23, applied as 0.1 wt % spray liquors, had a better fungicidal action (94%) than prior art active ingredient A (38%).

We claim:
1. An amine of the general formula I

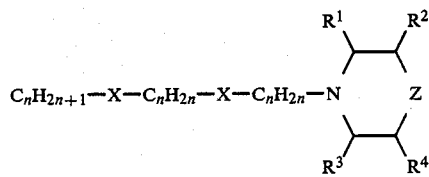

where n is an integer from 2 to 10, the individual values of n being identical or different, X is oxygen or sulfur, Z is oxygen or CH—$R_5$, and $R^1$, $R^2$, $R^3$, $R^4$ and $R^5$ are identical or different and are each hydrogen or $C_{1-2}$ alkyl, or a salt thereof.

2. A fungicide containing a solid or liquid carrier and a fungicidally effective amount of an amine of the formula

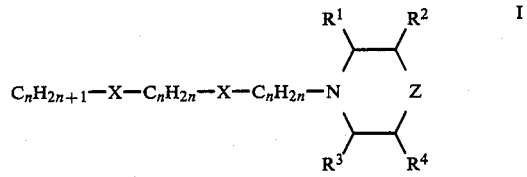

where n is an integer from 2 to 10, the individual values of n being identical or different, X is oxygen or sulfur, Z is oxygen or CH—$R_5$, and $R^1$, $R^2$, $R^3$, $R^4$ and $R^5$ are identical or different and are each hydrogen or $C_{1-2}$ alkyl, or a salt thereof.

3. A process for combating fungi, wherein the fungi, or the plants, soil or seed to be protected against fungus attack are treated with a fungicidally effective amount of an amine of the formula

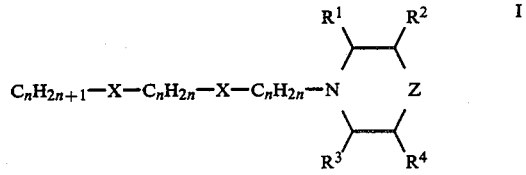

where n is an integer from 2 to 10, the individual values of n being identical or different, X is oxygen or sulfur, Z is oxygen or CH—$R_5$, and $R^1$, $R^2$, $R^4$ and $R^5$ are identical or different and are each hydrogen or $C_{1-2}$ alkyl, or a salt thereof.

4. A compound of the formula I as set forth in claim 1, where the radical $C_nH_{2n+1}$—X—$C_nH_{2n}$—X—$C_nH_{2n}$— is $(CH_3)_2CH$—$CH_2$—O—$(CH_2)_4$—O—$(CH_2)_4$— and $R^1$ and $R^3$ are hydrogen, $R^2$ and $R^4$ are methyl and Z is oxygen.

5. A compound of the formula I as set forth in claim 1, where the radical $C_nH_{2n+1}$—X—$C_nH_{2n}$—X—$C_nH_{2n}$— is $(CH_3)_2CH$—$CH_2$—O—$(CH_2)_5$—O—$(CH_2)_4$— and $R^1$ and $R^2$ are hydrogen, $R^2$ and $R^4$ are methyl and Z is oxygen.

* * * * *